(12) United States Patent
Tomita et al.

(10) Patent No.: US 7,316,901 B2
(45) Date of Patent: Jan. 8, 2008

(54) METHOD OF EFFICIENTLY DETECTING DOUBLE-STRANDED NUCLEIC ACID

(75) Inventors: Norihiro Tomita, Tochigi (JP); Yasuyoshi Mori, Tochigi (JP)

(73) Assignee: Eiken Kagaku Kabushiki Kaisha, Tokyo (JP)

( * ) Notice: Subject to any disclaimer, the term of this patent is extended or adjusted under 35 U.S.C. 154(b) by 535 days.

(21) Appl. No.: 10/481,369

(22) PCT Filed: Jun. 10, 2002

(86) PCT No.: PCT/JP02/05739

§ 371 (c)(1),
(2), (4) Date: Dec. 18, 2003

(87) PCT Pub. No.: WO02/103053

PCT Pub. Date: Dec. 27, 2002

(65) Prior Publication Data

US 2004/0171016 A1    Sep. 2, 2004

(30) Foreign Application Priority Data

Jun. 18, 2001   (JP) ............................. 2001-183716

(51) Int. Cl.
  *C12Q 1/68*   (2006.01)
  *C12P 19/34*   (2006.01)
(52) U.S. Cl. .......................... 435/6; 435/91.1; 435/91.2
(58) Field of Classification Search ..................... None
  See application file for complete search history.

(56) References Cited

U.S. PATENT DOCUMENTS 4,257,774 A * 3/1981 Richardson et al. ........ 436/508

5,998,135 A    12/1999 Rabbani et al.
6,297,008 B1 * 10/2001 Okamoto et al. .............. 435/6
2001/0014452 A1   8/2001 Makino et al.
2002/0068282 A1   6/2002 Okamoto et al.

FOREIGN PATENT DOCUMENTS

WO    WO 98/36096    8/1998

OTHER PUBLICATIONS

Ueda et al., (Sequence-specific DNA damage induced by reduced mitomycin C and 7-N-(p-hydroxyphenyl)mitomycin C. Nucleic Acids Res. (1984) 12:6673-6683).*
Cosa et al., (2001) "Photophysical properties of fluorescent DNA-dyes bound to single- and double stranded DNA in aqueous buffered solution," Photochemistry and Phtobiology, 73(6):585-599.
Notomi et al., (2000) "Loop-mediated isothermal amplification of DNA," Nucleic Acids Research, 28(12):e63.
Hanafi-Bagby et al. (2000) "Concentration dependence of a thiazole orange derivative that is used to determine nucleic acid hybridization by an optical biosensor" Analytica Chimica Acta 411:19-30.

* cited by examiner

*Primary Examiner*—Jeffrey Fredman
*Assistant Examiner*—David C. Thomas
(74) *Attorney, Agent, or Firm*—Fish & Richardson P.C.

(57) ABSTRACT

This invention relates to a method for efficiently detecting double-stranded nucleic acids. More particularly, this invention relates to a method for reducing signals derived from an intercalator bound to a single-stranded nucleic acid, wherein a compound that reacts more preferentially with an intercalator bound to a single-stranded nucleic acid than with an intercalator bound to a double-stranded nucleic acid or a compound that is bound to a single-stranded nucleic acid more strongly than an intercalator and is bound to a double-stranded nucleic acid more weakly than an intercalator is added to a mixture comprising double-stranded and single-stranded nucleic acids both having intercalators bound thereto, thereby reducing signals derived from an intercalator bound to a single-stranded nucleic acid.

15 Claims, 8 Drawing Sheets

SEQUENCE LISTING

```
<160> NUMBER OF SEQ ID NOS: 5

<210> SEQ ID NO 1
<211> LENGTH: 178
<212> TYPE: DNA
<213> ORGANISM: Artificial Sequence
<220> FEATURE:
<223> OTHER INFORMATION: synthetic DNA
```

```
<400> SEQUENCE: 1
tgcttgtggc ctctcgtggc agggcagtct gcggcggtgt tctggtgcac ccccagtggg      60
tcctcacagc tgcccactgc atcaggaaca aaagcgtgat cttgctgggt cggcacagcc     120
tgtttcatcc tgaagacaca ggccaggtat ttcaggtcag ccacagcttc acacaccc      178

<210> SEQ ID NO 2
<211> LENGTH: 44
<212> TYPE: DNA
<213> ORGANISM: Artificial Sequence
<220> FEATURE:
<223> OTHER INFORMATION: primer

<400> SEQUENCE: 2
tgttcctgat gcagtgggca gctttagtct gcggcggtgt tctg                       44

<210> SEQ ID NO 3
<211> LENGTH: 45
<212> TYPE: DNA
<213> ORGANISM: Artificial Sequence
<220> FEATURE:
<223> OTHER INFORMATION: primer

<400> SEQUENCE: 3
tgctgggtcg gcacagcctg aagctgacct gaaatacctg gcctg                      45

<210> SEQ ID NO 4
<211> LENGTH: 18
<212> TYPE: DNA
<213> ORGANISM: Artificial Sequence
<220> FEATURE:
<223> OTHER INFORMATION: primer

<400> SEQUENCE: 4
tgcttgtggc ctctcgtg                                                    18

<210> SEQ ID NO 5
<211> LENGTH: 17
<212> TYPE: DNA
<213> ORGANISM: Artificial Sequence
<220> FEATURE:
<223> OTHER INFORMATION: primer

<400> SEQUENCE: 5
gggtgtgtga agctgtg                                                     17
```

METHOD OF EFFICIENTLY DETECTING DOUBLE-STRANDED NUCLEIC ACID

TECHNICAL FIELD

The present invention relates to a method for detecting nucleic acids that can detect double-stranded nucleic acids using an intercalator with higher sensitivity.

BACKGROUND ART

The most general method for detecting the amplification product obtained by nucleic acid amplification such as polymerase chain reactions (PCR) is carried out by subjecting the solution after amplification to agarose gel electrophoresis and binding a fluorescent intercalator such as ethidium bromide thereto, and then observing specific fluorescence. When there is no possibility of contamination by other DNA and only the occurrence of the amplification product is of interest, fluorescence can be observed by adding a fluorescent intercalator to the solution after amplification while omitting electrophoresis. A fluorescent intercalator, however, binds to a single-stranded DNA such as a primer and emits fluorescence. Accordingly, a significant level of background noise can be contained in the detected fluorescent signal.

Recently, the present inventors have succeeded in developing a novel method for nucleic acid amplification, which does not require the complicated temperature control that is supposedly inevitable in PCR, i.e., the loop-mediated isothermal amplification (LAMP) method (Notomi, T. et al., Nucleic Acids Res. 28 (12), e63 (2000), WO 00/28082). In the LAMP method, the 3' terminal region of template polynucleotide is self-annealed, synthesis of complementary strands is started therefrom, and a primer that is annealed to the loop formed in the aforementioned synthesis is used in combination therewith. This enables the amplification under isothermal conditions, and has remarkably enhanced the simplicity of nucleic acid amplification.

In real-time monitoring of the product of nucleic acid amplification using a fluorescent intercalator, fluorescence intensity significantly varies in PCR since the product of nucleic acid amplification is repeatedly dissociated and reassociated due to thermal denaturation as a thermal cycle proceeds. In the LAMP method, however, fluorescence intensity does not vary since the reaction proceeds under isothermal conditions. Thus, the LAMP method is more suitable for real-time monitoring of the product of nucleic acid amplification. The LAMP method, however, requires approximately 10 times as many primers as the quantity required in PCR. When the product of nucleic acid amplification obtained by the LAMP method is intended to be detected using a fluorescent intercalator, the level of background noise caused by single-stranded primers, which are also present therein, is high. Thus, it is difficult to detect only the amplified double-stranded nucleic acids with high sensitivity.

An object of the present invention is to provide a process for detecting nucleic acids that can detect double-stranded nucleic acids using an intercalator with higher sensitivity by reducing signals derived from an intercalator bound to single-stranded nucleic acids.

The present inventors have conducted concentrated studies in order to attain the above object. As a result, they have succeeded in reducing signals derived from an intercalator bound to a single-stranded nucleic acid with the addition of a compound that reacts more preferentially with an intercalator bound to a single-stranded nucleic acid than with an intercalator bound to a double-stranded nucleic acid or a compound that is bound to a single-stranded nucleic acid more strongly than an intercalator and is bound to a double-stranded nucleic acid more weakly than an intercalator to a mixture comprising double-stranded and single-stranded nucleic acids both having intercalators bound thereto. This has led to the completion of the present invention.

More specifically, the present invention relates to a method for reducing signals derived from an intercalator bound to a single-stranded nucleic acid, wherein a compound that reacts more preferentially with an intercalator bound to a single-stranded nucleic acid than with an intercalator bound to a double-stranded nucleic acid is added to a mixture comprising double-stranded and single-stranded nucleic acids both having intercalators (e.g., ethidium bromide, acridine orange, TO-PRO-1® (Quinolinium, 4-[(3-methyl-2(3H)-benzothiazolylidene)methyl]-1-[3-(trimethylammonio)propyl]-, diiodide, or YO-PRO-1® (Quinolinium, 4-[(3-methyl-2(3H)-benzoxazolylidene)methyl]-1-[3-(trimethylammonio)propyl]-, diiodide) bound thereto, thereby reducing signals derived from an intercalator bound to a single-stranded nucleic acid. Examples of a compound that reacts more preferentially with an intercalator bound to a single-stranded nucleic acid than with an intercalator bound to a double-stranded nucleic acid include an oxidant, such as sodium hypochlorite, hydrogen peroxide, or potassium permanganate, and a reducer, such as sodium borohydride or sodium cyanoborohydride.

Further, the present invention relates to a method for reducing signals derived from an intercalator bound to a single-stranded nucleic acid, wherein a compound that is bound to a single-stranded nucleic acid more strongly than an intercalator and is bound to a double-stranded nucleic acid more weakly than an intercalator is added to a mixture comprising double-stranded and single-stranded nucleic acids both having intercalators (e.g., ethidium bromide, acridine orange, TO-PRO-1® (Quinolinium, 4-[(3-methyl-2(3H)-benzothiazolylidene)methyl]-1-[3-(trimethylammonio)propyl]-, diiodide), or YO-PRO-1® (Quinolinium, 4-[(3-methyl-2(3H)-benzoxazolylidene)methyl]-1-[3-(trimethylammonio)propyl]-, diiodide) bound thereto, thereby reducing signals derived from an intercalator bound to a single-stranded nucleic acid. An example of a compound that is bound to a single-stranded nucleic acid more strongly than an intercalator and is bound to a double-stranded nucleic acid more weakly than an intercalator is a second intercalator (e.g. methylene blue, actinomycin D, SYBR® Green 2 (CAS Registry No. 172827-25-7), or OliGreen® (CAS Registry No. 268220-33-3)) different from the above intercalator.

Furthermore, the present invention relates to a method for detecting a product of nucleic acid amplification comprising the following-steps:

(a) amplifying a nucleic acid through nucleic acid amplification;

(b) adding an intercalator to a reaction solution after the nucleic acid amplification;

(c) reducing signals derived from an intercalator bound to a single-stranded nucleic acid by any of the aforementioned methods; and (d) assaying the fluorescence intensity of a reaction solution.

Further, the present invention relates to a method for detecting a product of nucleic acid amplification comprising the following steps:

(a) amplifying a nucleic acid through nucleic acid amplification in the presence of an intercalator;

(b) reducing signals derived from an intercalator bound to a single-stranded nucleic acid by any of the aforementioned methods; and (c) assaying the fluorescence intensity of a reaction solution.

The present invention further relates to a method for detecting a product of nucleic acid amplification comprising the following steps:

(a) amplifying a nucleic acid through nucleic acid amplification in the presence of an intercalator and a compound that is bound to a single-stranded nucleic acid more strongly than an intercalator and is bound to a double-stranded nucleic acid more weakly than an intercalator; and (b) assaying the fluorescence intensity of a reaction solution.

The nucleic acid amplification can be carried out by the following steps:

(a) selecting a first arbitrary sequence F1c, a second arbitrary sequence F2c, and a third arbitrary sequence F3c in that order from the 3' terminus in a target region toward the 3' terminus on the polynucleotide chain and a fourth arbitrary sequence R1, a fifth arbitrary sequence R2, and a sixth arbitrary sequence R3 in that order from the 5' terminus in the target region toward the 5' terminus of the nucleotide chain;

(b) preparing a primer containing sequence F2 which is complementary to F2c and, on the 5' side of F2, the same sequence as F1c; a primer containing sequence F3 which is complementary to F3c; a primer containing the same sequence as R2 and, on the 5' side of the sequence, sequence R1c which is complementary to R1; and a primer containing the same sequence as R3; and (c) synthesizing DNA in the presence of a strand displacement-type polymerase and the primers using the nucleotide chain as a template.

The nucleic acid amplification can be carried out by the following steps:

(a) selecting a first arbitrary sequence F1c and a second arbitrary sequence F2c in that order from the 3' terminus in a target region toward the 3' terminus on the polynucleotide chain and a third arbitrary sequence R1 and a fourth arbitrary sequence R2 in that order from the 5' terminus in the target region toward the 5' terminus of the nucleotide chain;

(b) preparing a primer containing sequence F2 which is complementary to F2c and, on the 5' side of F2, the same sequence as F1c; and a primer containing the same sequence as R2 and, on the 5' side of the sequence, sequence R1c which is complementary to R1; and (c) synthesizing DNA in the presence of a strand displacement-type polymerase, the primers, and a melting temperature regulator (such as betaine or trimethylamine N-oxide) using the nucleotide chain as a template for amplification.

The present invention further relates to a kit for detecting double-stranded nucleic acids comprising, as elements, an intercalator (e.g, ethidiun, bromide, acridine orange, TO-PRO-1® (Quinolinium, 4-[(3-methyl-2(3H)-benzothiazolylidene)methyl]-1-[3-(trimethylammonio)propyl]-, diiodide), or YO-PRO-1® (Quinolinium, 4-[(3-methyl-2(3H)-benzoxazolylidene)methyl]-1-[3-(trimethylammonio) propyl]-, diiodide) and a compound that reacts more preferentially with an intercalator bound to a single-stranded nucleic acid than with an intercalator bound to a double-stranded nucleic acid and/or a compound that is bound to a single-stranded nucleic acid more strongly than an intercalator and is bound to a double-stranded nucleic acid more weakly than an intercalator. Examples of the compound that reacts more preferentially with an intercalator bound to a single-stranded nucleic acid than with an intercalator bound to a double-stranded nucleic acid include an oxidant such as sodium hypochlorite, hydrogen peroxide, or potassium permanganate, and a reducer, such as sodium borohydride or sodium cyanoborohydride. An example of the compound that is bound to a single-stranded nucleic acid more strongly than an intercalator and is bound to a double-stranded nucleic acid more weakly than an intercalator is a second intercalator (e.g. methylene blue, actinomycin D, SYBR® Green 2 (CAS Registry No. 172827-25-7), or OliGreen® (CAS Registry No. 268220-33-3)) different from the aforementioned intercalator.

DISCLOSURE OF THE INVENTION

The present invention is hereafter described in detail.

The present invention relates to a method for detecting double-stranded nucleic acids by detecting, with higher sensitivity, signals derived from an intercalator bound to a double-stranded nucleic acids through the reduction of signals derived from an intercalator bound to a single-stranded nucleic acid with the addition of a compound that reacts more preferentially with an intercalator bound to a single-stranded nucleic acid than with an intercalator bound to a double-stranded nucleic acid or a compound that is bound to a single-stranded nucleic acid more strongly than an intercalator and is bound to a double-stranded nucleic acid more weakly than an intercalator to a mixture comprising double-stranded and single-stranded nucleic acids both having intercalators bound thereto.

Accordingly, this method is particularly useful when selectively detecting amplification products when significant amounts of primers besides the amplified double-stranded nucleic acids remain in the reaction system during or after the nucleic acid amplification that utilizes primers as single-stranded nucleic acids.

In the present invention, the term "intercalator" refers to an intercalating agent, which is a compound that can be inserted (intercalated) in between adjacent planes formed by DNA nucleotide pairing. The term "signal" refers to a substance that functions as a marker for a specific substance or condition, such as fluorescence derived from an intercalator bound to a nucleic acid.

1. Nucleic Acid Amplification

Specifically, the present invention is useful when detecting an amplification product (double-stranded nucleic acid) obtained in the nucleic acid amplification that utilizes a primer, which is a single-stranded nucleic acid. Examples of nucleic acid amplification include, in addition to polymerase chain reaction (PCR), the LAMP method, the strand displacement amplification (SDA) method (JP Patent Publication (Kokoku) No. 7-114718 B (1995)), and the nucleic acid sequence based amplification (NASBA) method (JP Patent No. 2650159). More particularly, since a larger amount of primers are used in the LAMP method than in PCR, the amount of single-stranded primers remaining after the amplification is large. Accordingly, the method for detecting double-stranded nucleic acids according to the present invention is very useful when detecting amplification products obtained by the LAMP method.

In the LAMP method, a loop structure is formed at a terminus of the nucleotide sequence to be amplified and, simultaneously with elongation by polymerase starting therefrom, a primer hybridized in a region within the loop dissolves the elongation product into a single strand while elongating a nucleic acid chain by strand displacement. Since the generated single-stranded nucleic acid has a self-complementary region at its terminus, it forms a loop at the terminus, and new elongation is initiated. The actual LAMP method proceeds under isothermal conditions and, thus, the reactions described above occur simultaneously and in parallel. The LAMP method is characterized by a very large amount of the amplification product in addition to a strand displacement-type reaction that proceeds under isothermal conditions. One of the reasons for this is that the LAMP method does not involve thermal denaturation, which deactivates polymerase. The LAMP method is hereafter described.

(1) LAMP Method

At the outset, a scheme of the LAMP method is shown (FIG. 1 and FIG. 2). In the LAMP method, a template polynucleotide, which is the target of amplification, is prepared. The template polynucleotide (DNA or RNA) can be prepared by chemical synthesis, or, in accordance with conventional methods, from biological materials such as tissues or cells. The template polynucleotide is prepared so that suitable lengths of sequences (referred to as "bilateral sequences") are present on the sides (5' side and 3' side) in the target region for amplification (FIG. 1A). The term "bilateral sequence" refers to a sequence comprising a region from the 5' terminus in the target region to the 5' terminus of the polynucleotide chain and a sequence comprising a region from the 3' terminus in the target region to the 3' terminus of the polynucleotide chain (a portion indicated by two-headed arrows (← →) in FIG. 1A). The lengths of the bilateral sequences are 10 to 1,000 nucleotides, and preferably 30 to 500 nucleotides on the 5' side and the 3' side in the target region.

Predetermined regions are arbitrarily selected from the bilateral sequences in the template polynucleotide chain (FIG. 1A) containing the target region and the bilateral sequences. Specifically, a first arbitrary sequence F1c, a second arbitrary sequence F2c, and a third arbitrary sequence F3c are selected in that order from the 3' terminus in the target region toward the 3' terminus of the polynucleotide chain (FIG. 1B). Similarly, a fourth arbitrary sequence R1, a fifth arbitrary sequence R2, and a sixth arbitrary sequence R3 are selected in that order from the 5' terminus in the target region toward the 5' terminus of the polynucleotide chain (FIG. 1B). When selecting the arbitrary sequence F1c and the arbitrary sequence R1, the distance between F1c and R1 can be 0 nucleotides, i.e., contiguous. Alternatively, it can be selected in such a manner that F1c and R1 are allowed to partially overlap. The first to the sixth regions are respectively and arbitrarily selected in accordance with the sequences of prepared polynucleotide chains. Each region to be selected comprises preferably 5 to 100 nucleotides, and more preferably 10 to 50 nucleotides. Selection of the nucleotide length facilitates annealing of the primer described below.

Each of the arbitrary sequences is preferably selected so that, instead of intermolecular annealing, the amplification product obtained by the LAMP method preferentially initiates the intramolecular annealing between sequence F1c and sequence F1 and between sequence R1 and sequence R1c as shown in FIG. 2L, and forms a terminal loop structure. For example, in order to preferentially initiate the intramolecular annealing, it is important to consider the distance between sequence F1c and sequence F2c and the distance between sequence R1 and sequence R1c when selecting the arbitrary sequences. More specifically, both sequences are preferably located within a distance of 0 to 500 nucleotides, preferably 0 to 100 nucleotides, and most preferably 10 to 70 nucleotides. Numerical values respectively represent the number of nucleotides without containing sequences F1c and F2c and sequences R1 and R2.

Subsequently, a primer referred to as the "FA primer" is designed and synthesized, and this is annealed to F2c. The term "FA primer" includes sequence F2 which is complementary to region F2c and another sequence which is the same as F1c (this may be referred to as "F1c" for convenience). Examples thereof include those having a structure in which the 3'-terminus of sequence F1c is linked to the 5' side of F2 (FIG. 1C). The term "annealing" refers to the formation of a double-strand structure of a nucleotide chain through nucleotide pairing based on the Watson-Crick model. After the FA primer is annealed to sequence F2c on the template polynucleotide chain, DNA strand synthesis is initiated starting from F2 in the FA primer (FIG. 1D). Subsequently, a primer containing sequence F3, which is complementary to F3c (hereafter this may be referred to as "F3 primer"), is annealed to sequence F3c on the template polynucleotide chain (FIG. 1D). Strand displacement-type synthesis of DNA is then carried out starting from the annealed F3 primer (FIG. 1E). When a double-strand structure, which has been produced through the hybridization of a polynucleotide to a template for the synthesis of a complementary chain, is subjected to a reaction that synthesizes, starting from a primer, a complementary chain while separating the polynucleotide from the template, this process is termed "strand displacement-type synthesis of DNA." Specific examples thereof include a reaction in which synthesis proceeds so as to displace the chain synthesized by the FA primer with the chain synthesized by the F3 primer. In other words, the complementary chain of the template polynucleotide chain synthesized by the FA primer can be displaced by a chain elongated from the F3 primer in such a manner that the complementary chain is separated.

Two types of nucleotide chains, the following (i) and (ii), can be obtained by the above-described synthesis.

(i) A nucleotide chain containing sequence "(5')F3-F2-F1-target region-R1c-R2c-R3c(3')," which is complementary to sequence "(3')F3c-F2c-F1c-target region-R1-R2-R3 (5')" in the template polynucleotide chain (FIG. 1F).

(ii) A nucleotide chain formed into a single strand by displacement (separated), i.e., a nucleotide chain containing "(5')F1c-F2-F1-target region-R1c-R2c-R3c(3')" having the same sequence as F1c on its 5' terminal side (FIG. 1G).

F1 and F1c are complementary to each other in the nucleotide chain according to (ii) above and, thus, they hybridize to each other based on the intrachain hydrogen bonds between F1 and F1c, thereby forming a hairpin loop (FIG. 1G). F2 is contained in this hairpin loop.

Subsequently, a primer referred to as the "RA primer" is annealed to sequence R2c in the nucleotide chain according to (ii) above. In the RA primer, the 3' side of sequence R1c complementary to sequence R1 is linked to the 5' side of sequence R2. DNA strand synthesis is then initiated starting from the RA primer (FIG. 1H). When the elongated DNA synthesized starting from the RA primer has reached the end of the double-strand chain formed between F1 and F1c, the sequence of F1c is displaced with the elongated DNA in the same manner as the displacement shown in FIG. 1E (FIG. 1I). A primer containing sequence R3, which is complementary to sequence R3c (hereafter it may be referred to as the "R3 primer"), is then annealed to R3c of the template polynucleotide chain (FIG. 1I). Strand displacement-type synthesis of DNA is then carried out starting from the annealed R3 primer (FIG. 2J). Two types of nucleotide chains, i.e., the following (iii) and (iv), are synthesized based on the above synthesis.

(iii) A nucleotide chain "(3')F1-F2c-F1c-target region-R1-R2-R3(5')," which is complementary to sequence "(5')F1c-F2-F1-target region-R1c-R2c-R3c(3')" (FIG. 2K).

(iv) A nucleotide chain "(3')F1-F2c-F1-target region-R1-R2-R1c(3')" having F1 located closest to the 3' terminal side, and R1c located closest to the 5' terminal side (FIG. 2L).

The sequence according to (iv) above forms a hairpin loop by the intrachain hydrogen bonds between sequences F1 and F1c existing on the 3' side and between sequences R1 and R1c on the 5' side (FIG. 2L).

Subsequently, among the nucleotide chains according to (iv) above, region F2 of the FA primer is annealed to F2c in the hairpin loop portion on the 3' side (FIG. 2M). DNA strand synthesis is initiated starting from F1 annealed by the intrachain hydrogen bonds. In FIG. 1M, the elongation chain synthesized starting from F1 reaches the 5' terminus by opening the hairpin loop formed by R1-R2-R1c. In contrast, when a reaction proceeds starting from F2, a chain, which is complementary to a chain constituted by "F1c-target region-R1-R2-R1c," is synthesized. In this case, F1 and the chain "F1-target region-R1c-R2c-R1" synthesized starting from F1 are displaced by the chain that is synthesized starting from F2. This provides for double-stranded DNA having a single-strand protrusive construction denoted as "-target sequence-R1c-R2c-R1." The portion having a single-strand protrusive construction forms a hairpin loop by forming intrachain hydrogen bonds between R1c and R1 of a portion having a single-strand protrusive construction ("R1c-R2c-R1") (FIG. 2N). This construct initiates DNA strand synthesis starting from R1 annealed by the intrachain hydrogen bonds (FIG. 2N). Two types of nucleotide chains, the following (v) and (vi), are obtained based on the above synthesis.

(v) Sequence "(3')R1-R2-R1 c-target region-F1-F2-F1c-target region-R1-R2c-R1c-target region-F1-F2c-F1c-target region-R1-R2-R1c(5')" (FIG. 2O).

(vi) A sequence having F1c located closest to the 3' terminal side and R1 located closest to the 5' terminal side "(3')F1c-F2-F1-target region-R1c-R2c-R1(3')" (FIG. 2P).

The nucleotide chains according to (v) and (vi) above respectively form a hairpin loop having R2c as a loop portion and a hairpin loop having F2 and R2c as another loop portion by intrachain hydrogen bonds. The RA primer is annealed to the portion R2c forming the hairpin loop in two sequences, i.e., (v) and (vi) above, synthesis of DNA starting from the primer is initiated, and synthesis of nucleotides chain (complementary chain with sequence shown in (vi)) containing a target sequence proceeds. This complementary chain is the same as the sequence shown in FIG. 2L and, thus, the reactions according to FIGS. 2L to 2P are thereafter repeated. In contrast, the reaction from FIG. 1A can proceed and, thus, amplification of polynucleotide chain proceeds by repeating this series of syntheses.

The above-described amplification is carried out using four types of primers, i.e., the FA primer, the RA primer, the F3 primer, and the R3 primer. Alternatively, amplification under isothermal conditions can be initiated by using only two types of primers, the FA primer and the RA primer, without using the F3 primer and the R3 primer. In this alternative amplification, a melting temperature (Tm) regulator, for example, betaine or trimethylamine N-oxide (TMANO), should be present in the reaction system.

(2) Reaction Condition

In the reaction in accordance with the LAMP method, the ingredients below are added to a template single-stranded nucleic acid:

(i) four types of oligonucleotides (FA, RA, outer primer F3, and outer primer R3);

(ii) DNA polymerase for strand displacement-type synthesis of complementary chains; and (iii) a nucleotide serving as a substrate for DNA polymerase.

The reaction proceeds through incubation at such a temperature that stable nucleotide pairing between a nucleotide sequence constituting FA or RA and a complementary nucleotide sequence thereof can be formed, and enzyme activity can be maintained. The incubation temperature is 50 to 75° C., and preferably 55 to 70° C. The incubation time is 1 minute to 10 hours, and preferably 5 minutes to 4 hours.

In the LAMP method according to the above two embodiments, the FA primer and the RA primer are also referred to as "inner primers" and the F3 primer and the R3 primer are also referred to as "outer primers."

Synthesis of nucleotide chains from the outer primer should be initiated after synthesis of nucleotide chains from the inner primer. A method for satisfying this condition includes the one which sets the concentration of the inner primer higher than that of the outer primer. More specifically, the concentration of the inner primer can be set higher than that of the outer primer by 2- to 50-fold, and preferably by 4- to 25-fold.

Polymerase, which catalyzes the strand displacement-type synthesis of complementary chains (this may be referred to as "strand displacement-type polymerase), includes Bst DNA polymerase, Bca(exo-) DNA polymerase, the Klenow fragment of E. coli DNA polymerase I, Vent DNA polymerase, Vent(Exo-) DNA polymerase (exonuclease activity is removed from Vent DNA polymerase), DeepVent DNA polymerase, DeepVent(Exo-) DNA polymerase (exonuclease activity is removed from DeepVent DNA polymerase), φ29 phage DNA polymerase, MS-2 phage DNA polymerase, Z-Taq DNA polymerase (Takara Shuzo Co., Ltd.), and KOD DNA polymerase (Toyobo Co., Ltd.).

This reaction is conducted in the presence of, for example, a buffer giving suitable pH to the enzyme reaction, salts necessary for maintaining the catalytic activity of the enzyme or for annealing, a protective agent for the enzyme, and, if necessary, a regulator for melting temperature (Tm). A buffer, such as Tris-HCl having a buffering action in the range of weakly alkaline to neutral, is used. The pH is adjusted depending on the DNA polymerase being used. As salts, $MgCl_2$, KCl, NaCl, $(NH_4)_2SO_4$, etc. are suitably added to maintain the activity of the enzyme and to regulate the melting temperature (Tm) of the nucleic acid. Bovine serum albumin or sugars can be used as protective agents for enzymes. Further, betaine (N,N,N-trimethylglycine), trimethylamine N-oxide (TMANO), dimethyl sulfoxide (DMSO), or formamide is used as a regulator for melting temperature (Tm). By the use of the regulator for melting temperature (Tm), annealing of the oligonucleotide can be regulated under restricted temperature conditions. In particular, betaine and trimethylamine N-oxide (TMANO) are also effective for improving the efficiency of strand displacement by virtue of its isostabilization properties. By adding betaine in an amount of 0.2 to 3.0 M, and preferably about 0.5 to 1.5 M to the reaction solution, its promoting action on the nucleic acid amplification of the present invention can be expected. Because these regulators for melting temperature act to lower melting temperature, conditions giving suitable stringency and reactivity must be empirically determined in consideration of other reaction conditions such as concentration of salts and reaction temperature.

2. Methods for Reducing Signals Derived from an Intercalator Bound to a Single-stranded Nucleic Acid The following methods are examples of methods for reducing signals derived from an intercalator bound to a single-stranded nucleic acid in a mixture comprising double-stranded and single-stranded nucleic acids both having intercalators bound thereto.

(1) A Method in Which a Compound that Reacts More Preferentially with an Intercalator Bound to a Single-stranded Nucleic Acid than with an Intercalator Bound to a Double-stranded Nucleic Acid is Added (1)-1 Utilization of an Oxidant or Reducer A compound that reacts more preferentially with an intercalator bound to a single-stranded nucleic acid than with an intercalator bound to a double-stranded nucleic acid is added to a mixture comprising double-stranded and single-stranded nucleic acids having intercalators bound thereto. This can reduce signals derived from an intercalator bound to a single-stranded nucleic acid. An example eta compound that reacts more preferentially with an intercalator bound to a single-stranded nucleic acid than with an intercalator bound to a double-stranded nucleic acid is an oxidant or reducer. Specifically, an oxidant or reducer is further added to a mixed solution of double-stranded and single-stranded nucleic acids that is stained by the addition of an intercalator, and the resultant is maintained at suitable temperature for a suitable period of time. Thus, the intercalator bound to single-stranded nucleic acids is preferentially oxidized or reduced compared with the intercalator bound to double-stranded nucleic acids. This lowers fluorescence intensity derived from the intercalator bound to a single strand. Examples of an intercalator include ethidium bromide, acridine orange, TO-PRO-1® (Quinolinium, 4-[(3-methyl-2(3H)-benzothiazolylidene)methyl]-1-[3-(trimethylammonio)propyl]-, diiodide), and YO-PRO-1® (Quinolinium, 4-[(3-methyl-2(3H)benzoxazolylidene)methyl]-1-[3-(trimethylammonio)propyl]-, diiodide. Examples of an oxidant include sodium hypochlorite. (NaClO), hydrogen peroxide ($H_2O_2$), and potassium permanganate ($KMnO_4$). Examples of a reducer include sodium borohydride ($NaBH_4$) and sodium cyanoborohydride ($NaBH_3CN$).

When detecting a product of nucleic acid amplification by this method, fluorescence intensity is generally assayed through addition of an intercalator to the reaction solution after the nucleic acid amplification, followed by further addition of an oxidant or reducer. Alternatively, an intercalator is added to the reaction solution before the nucleic acid amplification, amplification is carried out in the presence of the intercalator, and an oxidant or reducer is added after the reaction, thereby assaying the fluorescence intensity.

(1)-2 Utilization of a Complex-forming Compound

A compound that forms a complex with an intercalator can be used as a compound that reacts more preferentially with an intercalator bound to a single-stranded nucleic acid than with an intercalator bound to a double-stranded nucleic acid. Specifically, an intercalator and the complex-forming compound are added to a mixed solution of double-stranded and single-stranded nucleic acids, and the resultant is maintained at suitable temperature for a suitable period of time. A weak bond between a single-stranded nucleic acid and an intercalator is preferentially inhibited by the complex-forming reaction compared with a bond between a double-stranded nucleic acid and an intercalator. This lowers fluorescence intensity derived from an intercalator bound to a single strand. An example of a combination of an intercalator and a complex-forming compound is that of methylene blue (an intercalator) and Acid Orange 7 (a complex-forming compound).

When detecting a product of nucleic acid amplification by this method, fluorescence intensity is generally assayed through simultaneous or sequential addition of an intercalator and a complex-forming compound to the reaction solution after the nucleic acid amplification. Alternatively, an intercalator is added to the reaction solution before the nucleic acid amplification, amplification is carried out in the presence of the intercalator, and a complex-forming compound is added after the reaction, thereby assaying the fluorescence intensity.

Absorbance may be assayed instead of fluorescence intensity by utilizing differences in the absorption spectrum caused by the complex formation. That is, since the absorption spectrum of an intercalator differs from that of the complex thereof, it is possible to quantitatively assay only the intercalator that did not form a complex.

(2) A Method in Which a Compound that is Bound to a Single-stranded Nucleic Acid More Strongly than an Intercalator and is Bound to a Double-stranded Nucleic Acid More Weakly than an Intercalator is Added A compound that is bound to a single-stranded nucleic acid more strongly than an intercalator and is bound to a double-stranded nucleic acid more weakly than an intercalator is added to a mixture comprising double-stranded and single-stranded nucleic acids both having intercalators bound thereto. This can reduce signals derived from an intercalator bound to a single-stranded nucleic acid. An example of a compound that is bound to a single-stranded nucleic acid more strongly than an intercalator and is bound to a double-stranded nucleic acid more weakly than an intercalator is a second intercalator that is different from the aforementioned intercalator (hereafter referred to as a "first intercalator"). A second intercalator different from the first intercalator that is bound to a single-stranded nucleic acid more strongly than the first intercalator and is bound to a double-stranded nucleic acid more weakly than the first intercalator is added to a mixed solution of double-stranded and single-stranded solution which is stained by the addition of the first intercalator, and the resultant is maintained at suitable temperature for a suitable period of time. Thus, the first intercalator bound to a single-stranded nucleic acid is preferentially displaced by the second intercalator compared with the first intercalator bound to a double-stranded nucleic acid. This lowers fluorescence intensity derived from the first intercalator bound to a single strand. Examples of the first intercalator that is first added to a mixture of double-stranded and single-stranded nucleic acids include ethidium bromide, acridine orange, TO-PRO-1® (Quinolinium, 4-[(3-methyl-2(3H)-benzothiazolylidene)methyl]-1-[3-(trimethylammonio)propyl]-, diiodide), and YO-PRO-1® (Quinolinium, 4-[(3-methyl-2(3H)-benzoxazolylidene)methyl]-1-[3-(trimethylammonio)propyl]-, diiodide. Examples of the second intercalator, which is added for the preferential displacement with the first intercalator bound to a single-stranded nucleic acid and is different from the first intercalator, include methylene blue, actinomycin D, SYBR® Green 2 (CAS Registry No. 172827-25-7), and OliGreen® (CAS Registry No. 268220-33-3).

When detecting a product of nucleic acid amplification by this method, fluorescence intensity is generally assayed through addition of an intercalator to the reaction solution after the nucleic acid amplification, followed by further addition of the second intercalator different from the aforementioned intercalator. Alternatively, an intercalator is added to the reaction solution before the nucleic acid amplification, amplification is carried out in the presence of the intercalator, and the second intercalator different from the aforementioned intercalator is added after the reaction, thereby assaying the fluorescence intensity. Further, the two above types of intercalators are previously added to the reaction solution before the nucleic acid amplification, amplification is carried out in the presence of the two types of intercalators, and fluorescence intensity can be assayed after the reaction.

3. Detection of Double-stranded Nucleic Acids

In the present invention, double-stranded nucleic acids are detected by assaying the fluorescence emitted from the intercalator bound to nucleic acids using a fluorophotometer after the process described in 2 above. For example, when detecting the amplification product obtained in the reaction in 1 above, a reaction system in which amplification was carried out without template DNA (control system 1) or a reaction system without DNA polymerase (control system 2) is provided as a control. The aforementioned control system and a system in which amplification was carried out as usual in the presence of template DNA and DNA polymerase (a test system) are subjected to the process as described in 2 above, and differences in fluorescence intensity between the control system and the test system are inspected. Thus, the generation of the amplification product in the reaction solution through the reaction can be confirmed. More specifically, when fluorescence intensity of the test system is greater than that of the control system 1 or 2, it can be evaluated that the amplification product was detected in the test system.

An example of a fluorophotometer that can be used for assaying fluorescence intensity is the ABI PRISM 7700 sequence detection system (PE Applied Biosystems). When assaying fluorescence intensity, the excitation wavelength and the assay wavelength are suitably determined in accordance with the type of intercalator used for staining nucleic acids. In the present invention, the reaction solution after the initiation of amplification is subjected to the process described in 2 above, and fluorescence intensity thereof is then assayed with the elapse of time. Thus, transition in the conditions of the reaction product with the elapse of the reaction time can be monitored.

4. Kit for Detecting or Monitoring Double-stranded Nucleic Acids

In the method for detecting or monitoring the product of nucleic acid amplification according to 3 above, reagents necessary for implementation can be packaged and supplied as a kit Specific examples include a kit comprising the following elements.

[Elements of Kit]

(1) An intercalator (for example, ethidium bromide, acridine orange, TO-PRO-1® (Quinolinium, 4-[(3-methyl-2 (3H)-benzothiazolylidene)methyl]-1-[3-(trimethylammonio)propyl]-, diiodide), and YO-PRO-1® (Quinolinium, 4-[(3-methyl-2(3H)-benzoxazolylidene)methyl]-1-[3-(trimethylammonio)propyl]-, diiodide);

(2) a compound that reacts more preferentially with an intercalator bound to a single-stranded nucleic acid than with an intercalator bound to a double-stranded nucleic acid (for example, an oxidant such as sodium hypochlorite (NaClO), hydrogen peroxide ($H_2O_2$), or potassium permanganate ($KMnO_4$) and a reducer such as sodium borohydride); and (3) a compound tat is bound to a single-stranded nucleic acid more strongly than an intercalator and is bound to a double-stranded nucleic acid more weakly than an intercalator (for example, the second intercalator different from the intercalator that was first added to a mixed solution of double-stranded and single-stranded nucleic acids such as methylene blue, actinomycin D, SYBR® Green 2 (CAS Registry No. 172827-25-7), or OliGreen® (CAS Registry No. 268220-33-3)).

This kit can also be used for amplifying and detecting a target nucleic acid based on the LAMP method by adding the elements below:

[Elements that Can be Added]

(a) when a first arbitrary sequence F1c, a second arbitrary sequence F2c, and a third arbitrary sequence F3c are selected in that order from the 3' terminus in the target region toward the 3' terminus of the polynucleotide chain that constitutes a nucleic acid to be detected and a fourth arbitrary sequence R1, a fifth arbitrary sequence R2, and a sixth arbitrary sequence R3 are selected in that order from the 5' terminus in the target region toward the 5' terminus of the polynucleotide chain, a primer containing sequence F2 which is complementary to F2c and, on the 5' side of F2, the same sequence as F1c; a primer containing sequence F3 which is complementary to F3c; a primer containing the same sequence as R2 and, on the 5' side of the sequence, sequence R1c which is complementary to R1; and a primer containing the same sequence as R3;

(b) a polymerase catalyzing strand displacement-type synthesis of complementary chains; and (c) a nucleotide serving as a substrate for the synthesis of complementary strands.

The elements of the kit can vary according to the embodiment of the LAMP method to be employed. Specifically, a primer containing the sequence F3 which is complementary to arbitrary sequence F3c and a primer containing the same sequence as arbitrary sequence R3 can be optionally omitted from the elements. In such a case, a melting temperature regulator (for example, betaine or trimethylamine N-oxide) is preferably added. Further, a buffer providing suitable conditions for the enzyme reaction and reagents necessary for detecting the reaction product of synthesis may be optionally added. According to a preferred embodiment of the present invention, reagents necessary for one reaction can be supplied in the state of being fractionated into reaction vessels.

Figure 1:
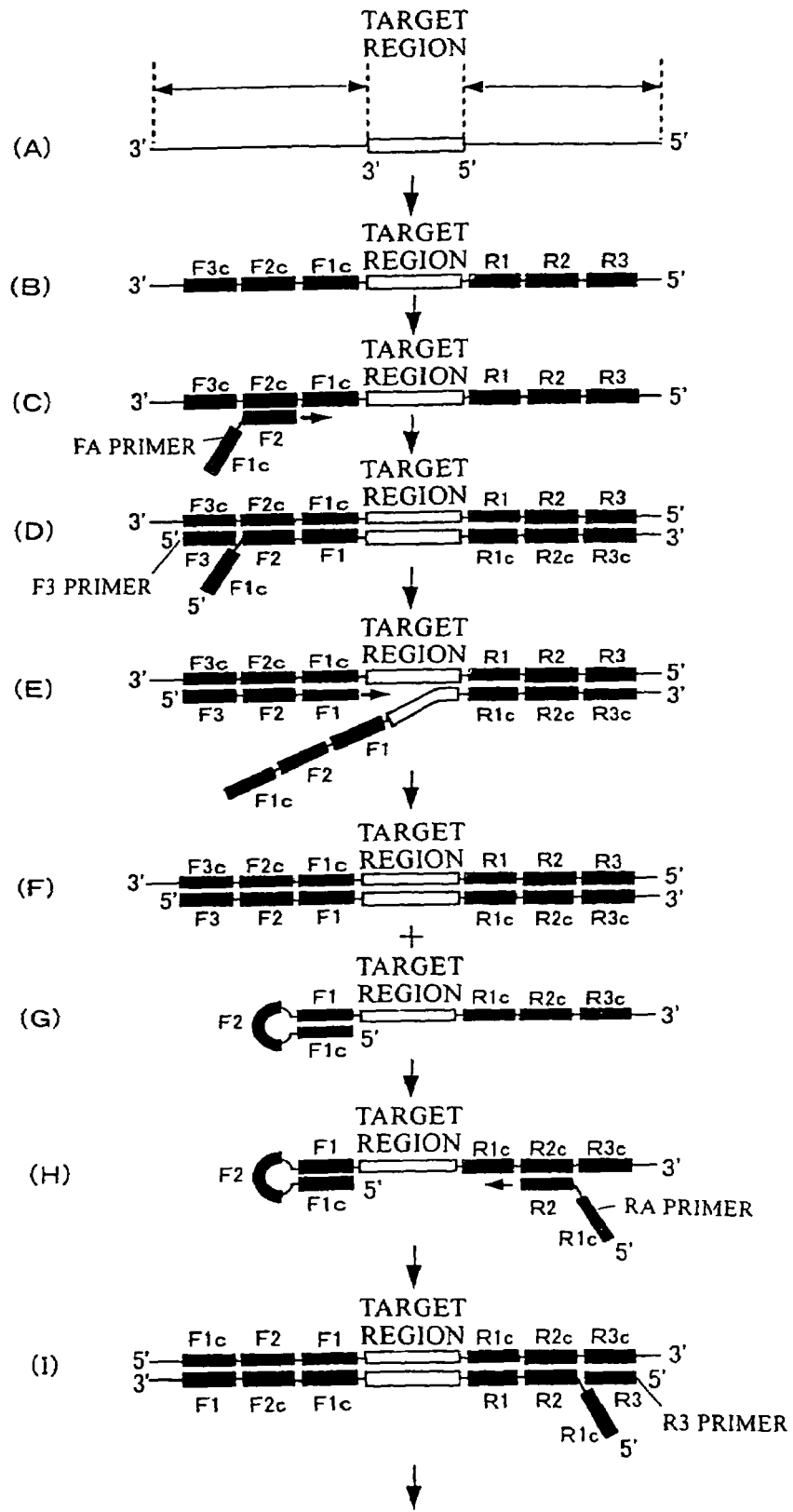
FIG. 1 shows a scheme of amplification by the LAMP method.
Figure 2:
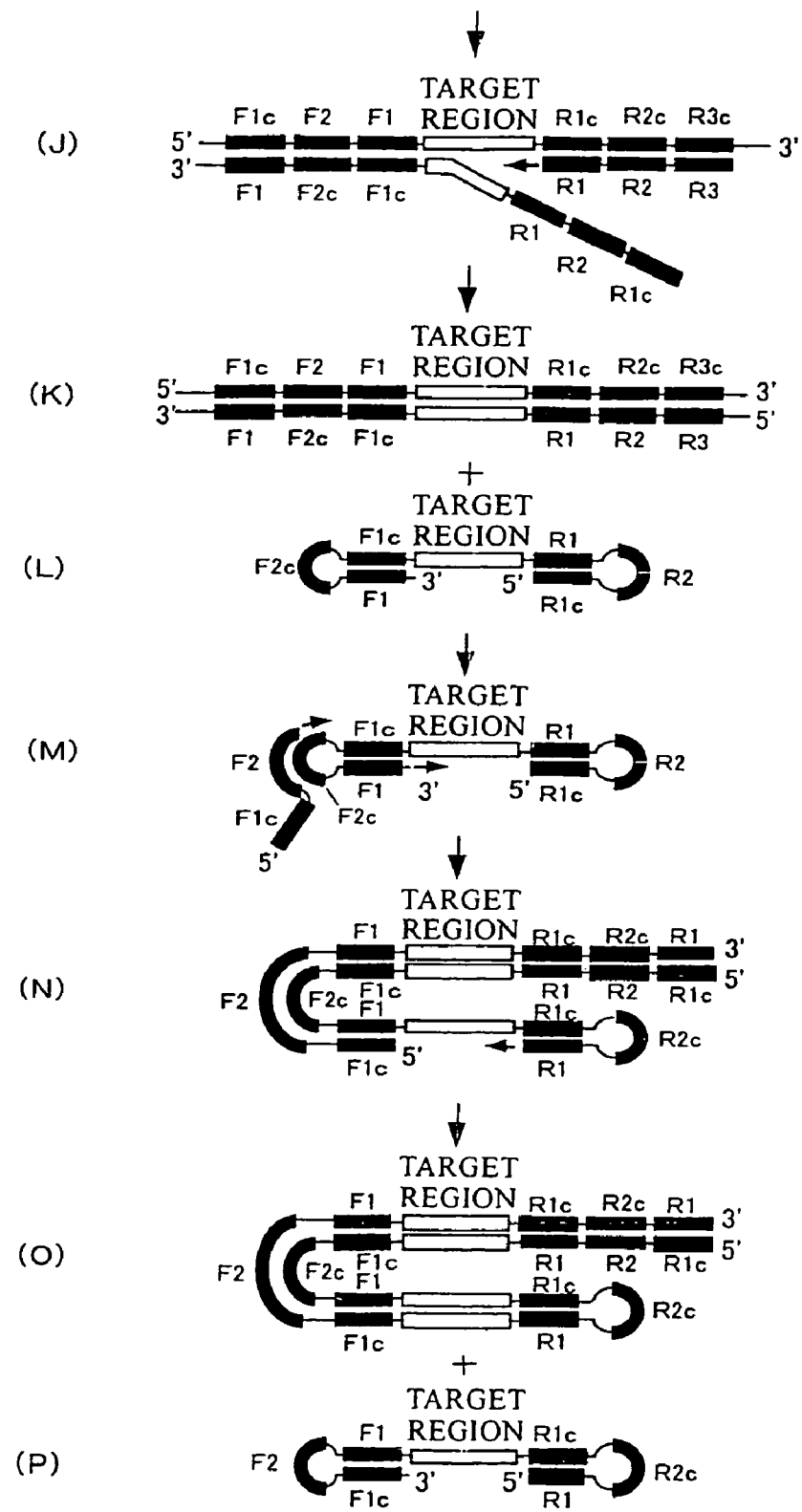
FIG. 2 shows a scheme of amplification by the LAMP method.

This description includes part or all of the contents as disclosed in the description of Japanese Patent Application No. 2001-183716, which is a priority document of the present application.

BEST MODE FOR CARRYING OUT THE INVENTION

The present invention will be described in more detail with reference to the following examples, although the technical scope of the present invention is not limited to these examples.

EXAMPLE 1

Effect of an Oxidant or Reducer On the Detection of the Lamp Reaction Product Using Ethidium Bromide (1) Nucleic Acid Amplification by the LAMP Method

TABLE 1

| Composition of reaction solution |
| --- |
| Composition of reaction solution (in 25 μL) |
| 20 mM Tris-HCl pH 8.8 |
| 10 mM KCl |
| 10 mM (NH$_4$)$_2$SO$_4$ |
| 4 mM MgSO$_4$ |
| 0.1% Tween 20 |
| 0.4 mM dNTP |
| 8 U Bst DNA polymerase (NEB) |
| 1.6 μM FA primer |
| 1.6 μM RA primer |
| 0.4 μM F3 primer |
| 0.4 μM R3 primer |

To the above reaction solution, $6 \times 10^{-20}$ mol of DNA of prostate-specific antigen (PSA) as a template for the LAMP reaction and ethidium bromide (EtBr, 0.5 μ/ml) for detecting amplification products were added. Amplification was then carried out at 65° C. for 30 minutes. The reaction solution to which template DNA had been added was determined to be a positive reaction solution, and the reaction solution without the addition of template DNA was determined to be a negative reaction solution. In this amplification, the following sequence (SEQ ID NO: 1) included in the template was determined to be a polynucleotide of interest.

5'-TGCTTGTGGCCTCTCGTGGCAGGGCAGTCTGCG (SEQ ID NO: 1)

GCGGTGTTCTGGTGCACCCCCAGTGGGTCCTCACAG

-continued

CTGCCCACTGCATCAGGAACAAAAGCGTGATCTTGC

TGGGTCGGCACAGCCTGTTTCATCCTGAAGACACAG

GCCAGGTATTTCAGGTCAGCCACAGCTTCACACACC

C-3'

Inner primers (FA primer and RA primer) and outer primers (F3 primer and R3 primer) in the reaction solution were designed as follows based on the nucleotide sequence as shown in SEQ ID NO: 1.

[Inner primers]

FA primer
5'-TGTTCCTGATGCAGTGGGCAGCTTTAGTCTGCG (SEQ ID NO: 2)
GCGGTGTTCTG-3'

RA primer
5'-TGCTGGGTCGGCACAGCCTGAAGCTGACCTGAA (SEQ ID NO: 3)
ATACCTGGCCTG-3'

[Outer primers]

F3 primer
5'-TGCTTGTGGCCTCTCGTG-3'         (SEQ ID NO: 4)

R3 primer
5'-GGGTGTGTGAAGCTGTG-3'          (SEQ ID NO: 5)

(2) Oxidation or Reduction

The positive and the negative reaction solutions after the amplification were subjected to oxidation or reduction. Specifically, oxidation was carried out by adding sodium hypochlorite (NaClO) to the both reaction solutions to concentrations of 2.8% and maintaining the resultant at room temperature for 2 hours. Reduction was carried out by adding 4 mM sodium borohydride (NaBH$_4$) and 0.4 mM sodium hydroxide (NaOH) to the both reaction solutions and maintaining the resultant on ice for 10 minutes. After the reaction, the fluorescence intensity of each reaction solution was assayed using the ABI PRISM® 7700 sequence detection system (PE Applied Biosystems) at an excitation wavelength of 488 nm and an assay wavelength of 605 nm.

Figure 3:
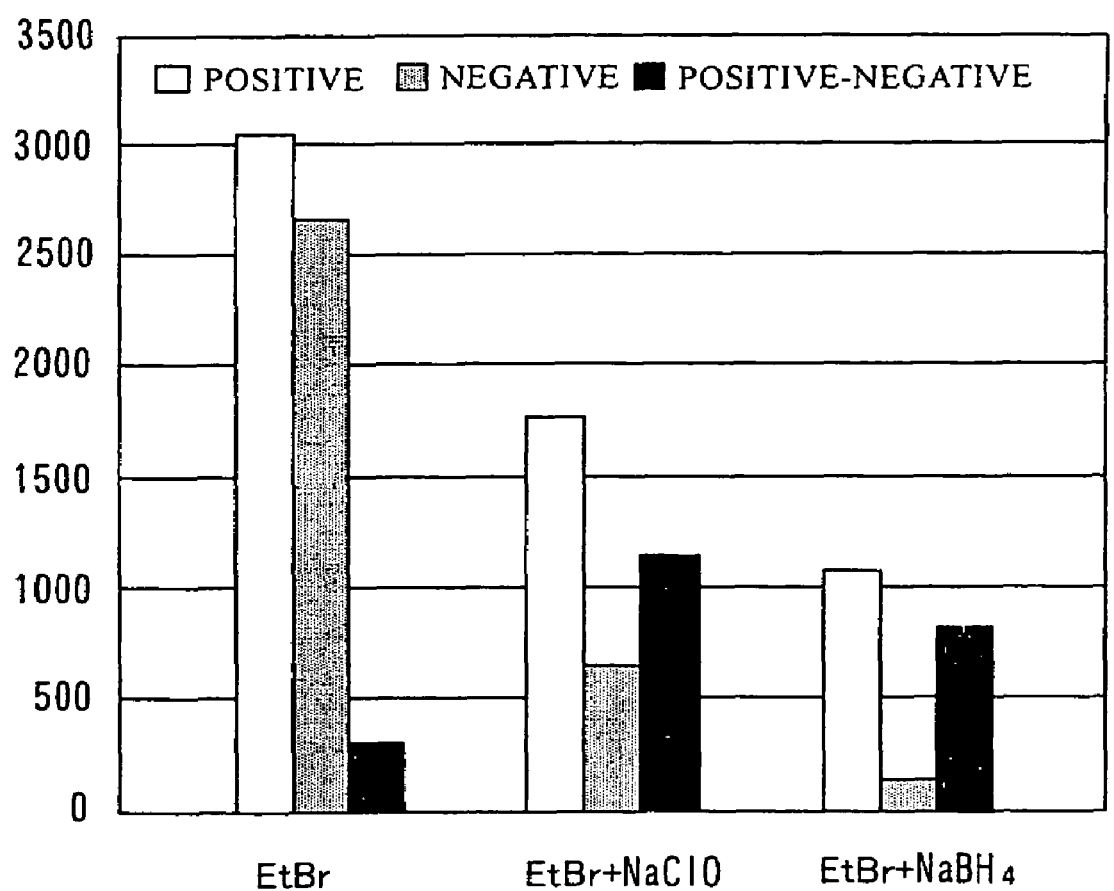
FIG. 3 shows fluorescence intensity of each reaction solution when the LAMP reaction is carried out in the presence of ethidium bromide, followed by the addition of a reducer or oxidant.

The assay results are shown in FIG. 3. In the case of the reaction solutions which were not subjected to oxidation or reduction (EtBr in FIG. 3), the fluorescence intensity of the positive reaction solution was 3,012, and that of the negative reaction solution was 2,695. That is, difference in the fluorescence intensity resulting from the occurrence of products of double-stranded nucleic acid amplification was 317. In contrast, in the case of the reaction solutions which were subjected to oxidation using sodium hypochlorite (EtBr+ NaClO in FIG. 3), the fluorescence intensity of the positive reaction solution was 1,784, and that of the negative reaction solution was 648. That is, difference in the fluorescence intensity resulting from the occurrence of products of double-stranded nucleic acid amplification was as large as 1,136. In the case of the reaction solutions which were subjected to reduction using sodium borohydride (EtBr+ NaBH$_4$ in FIG. 3), the fluorescence intensity of the positive reaction solution was 1,051, and that of the negative reaction solution was 218. That is, difference in the fluorescence intensity resulting from the occurrence of products of double-stranded nucleic acid amplification was as large as 833.

Thus, sensitivity for detecting products of double-stranded nucleic acid amplification using ethidium bromide can be enhanced by oxidizing or reducing the amplification products stained with ethidium bromide.

EXAMPLE 2

Figure 4:
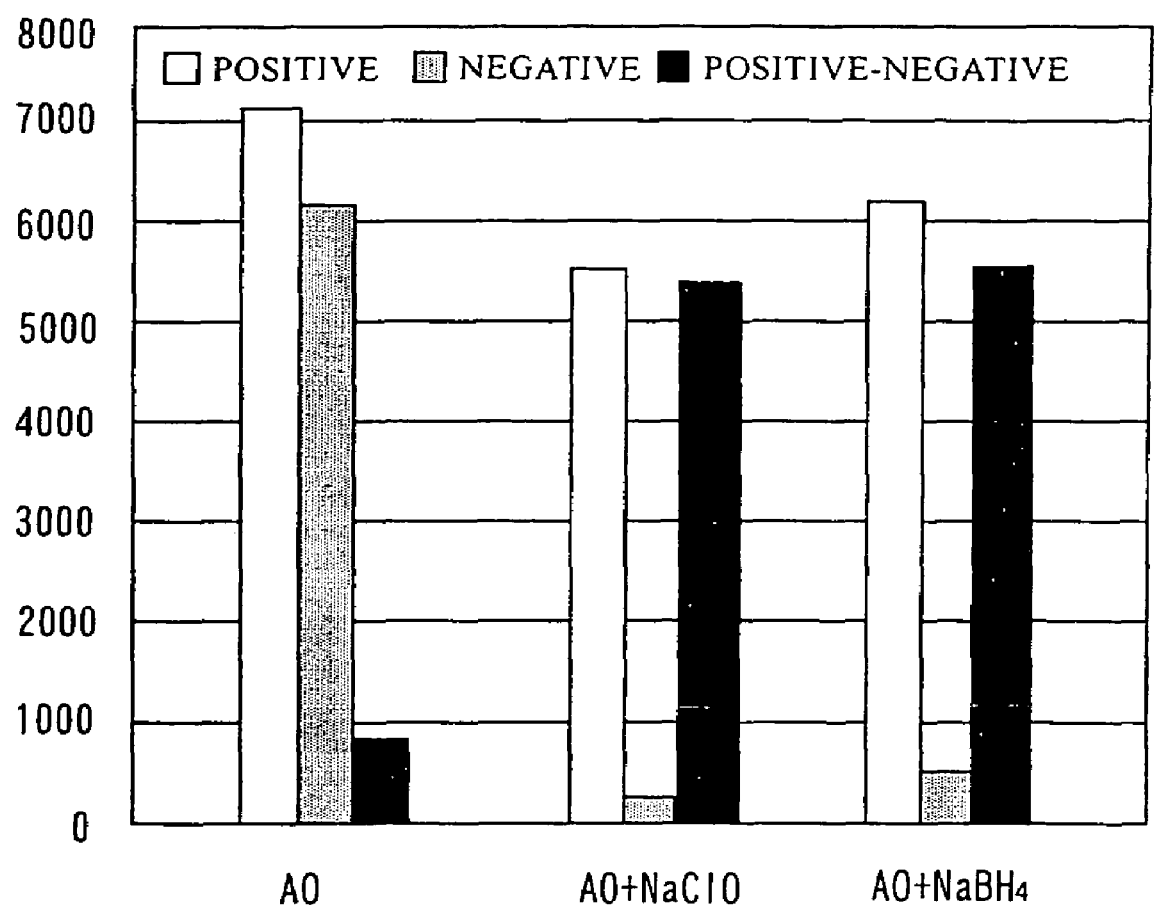
FIG. 4 shows fluorescence intensity of each reaction solution when the LAMP reaction is carried out in the presence of acridine orange, followed by the addition of a reducer or oxidant.

Effect of an Oxidant or Reducer on the Detection of the LAMP Reaction Product Using Acridine Orange The effects of an oxidant or reducer on the efficiency of detecting the LAMP reaction product were inspected under the same experimental conditions as used in Example 1 except that acridine orange was added instead of ethidium bromide and the assay wavelength was set at 575 nm in the amplification of nucleic acids described in Example 1. The assay results are shown in FIG. 4. In the case of the reaction solutions which were not subjected to oxidation or reduction (AO in FIG. 4), the fluorescence intensity of the positive reaction solution was 7,053, and that of the negative reaction solution was 6,155. That is, difference in the fluorescence intensity resulting from the occurrence of products of double-stranded nucleic acid amplification was 898. In contrast, in the case of the reaction solutions which were subjected to oxidation using sodium hypochlorite (AO+ NaClO in FIG. 4), the fluorescence intensity of the positive reaction solution was 5,521, and that of the negative reaction solution was 201. That is, difference in the fluorescence intensity resulting from the occurrence of products of double-stranded nucleic acid amplification was as large as 5,320. In the case of the reaction solutions which were subjected to reduction using sodium borohydride (AO+ NaBH$_4$ in FIG. 4), the fluorescence intensity of the positive reaction solution was 6,214, and that of the negative reaction solution was 596. That is, difference in the fluorescence intensity resulting from the occurrence of products of double-stranded nucleic acid amplification was as large as 5,618.

Thus, sensitivity for detecting products of double-stranded nucleic acid amplification using acridine orange can be enhanced by oxidizing or reducing the amplification products stained with acridine orange.

EXAMPLE 3

Figure 5:
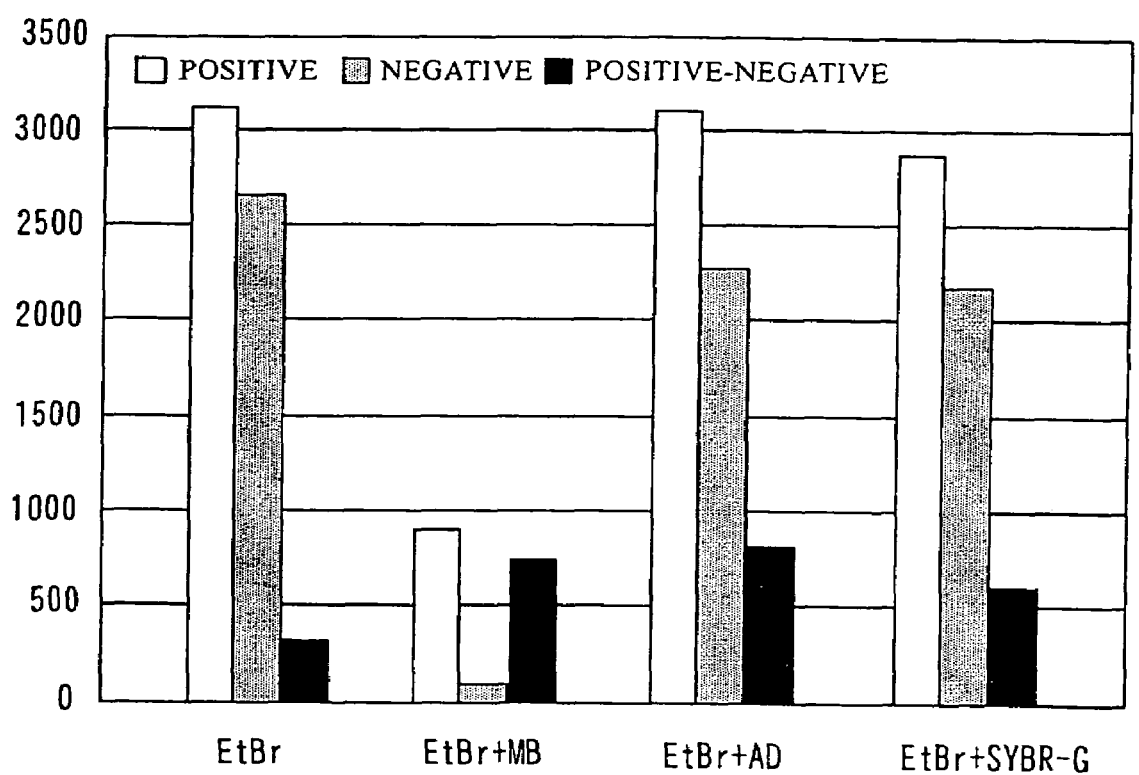
FIG. 5 shows fluorescence intensity of each reaction solution when the LAMP reaction is carried out by adding the second intercalator in addition to ethidium bromide.

Effect of Another Intercalator On the Detection of the LAMP Reaction Product Using Ethidium Bromide The LAMP reaction was carried out under the same reaction conditions as in Example 1 except that, in addition to ethidium bromide, 20 μM of methylene blue, 1 μg/ml of actinomycin D, or 100,000-fold diluted SYBR® Green 2 (Molecular Probes) was added as the second intercalator. Thus, effects of each of the aforementioned second intercalators on the efficiency of detecting the LAMP reaction product were inspected. The results are shown in FIG. 5. In the case of the reaction solutions to which the second intercalator was not added in addition to ethidium bromide (EtBr in FIG. 5), the fluorescence intensity of the positive reaction solution was 3,085, and that of the negative reaction solution was 2,701. That is, difference in the fluorescence intensity resulting from the occurrence of products of double-stranded nucleic acid amplification was 384. In contrast, in the case of the reaction solutions to which methylene blue was added (EtBr+MB in FIG. 5), the fluorescence intensity of the positive reaction solution was 860, and that of the negative reaction solution was 116. That is, difference in the fluorescence intensity resulting from the occurrence of products of double-stranded nucleic acid amplification was as Large as 744. In the case of the reaction solutions to which actinomycin D was added (EtBr+AD in FIG. 5), the fluorescence intensity of the positive reaction solution was 3,158, and that of the negative reaction solution was 2,322. That is, difference in the fluorescence intensity resulting from the occurrence of products of double-stranded nucleic acid amplification was as large as 836. Further, in the case of the reaction solutions to which SYBR® Green 2 was added (EtBr+SYBR-G in FIG. 5), the fluorescence intensity of the positive reaction solution was 2,822, and that of the negative reaction solution was 2,268. That is, difference in the fluorescence intensity resulting from the occurrence of products of double-stranded nucleic acid amplification was as large as 554.

Thus, sensitivity for detecting products of double-stranded nucleic acid amplification using ethidium bromide can be enhanced by performing the LAMP reaction in the presence of the second intercalator together with ethidium bromide.

EXAMPLE 4

Figure 6:
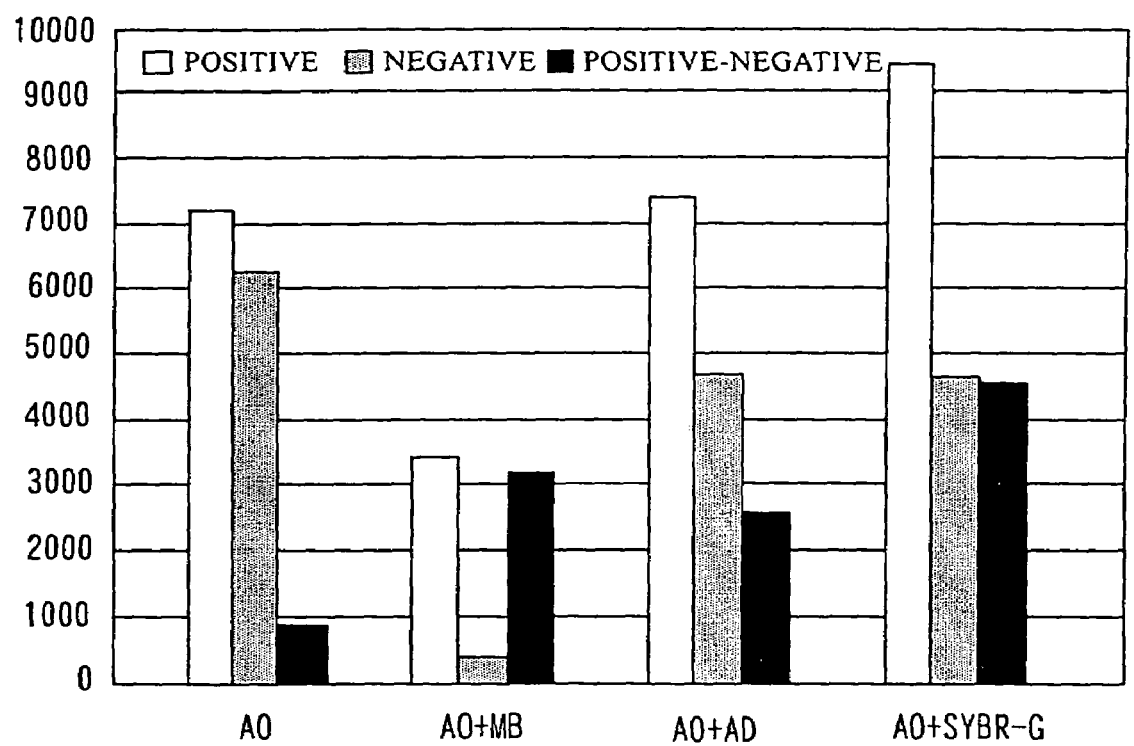
FIG. 6 shows fluorescence intensity of each reaction solution when the LAMP reaction is carried out by adding the second intercalator in addition to acridine orange.

Effect of Another Intercalator On the Detection of the LAMP Reaction Product Using Acridine Orange The LAMP reaction was carried out under the same reaction conditions as in Example 1 except that, in addition to acridine orange that was added instead of ethidium bromide, 20 μM of methylene blue, 1 μg/ml of actinomycin D, or 100,000-fold diluted SYBR® Green 2 (Molecular Probes) was added as the second intercalator and the assay wavelength was set at 575 nm. Thus, effect of each intercalator on the efficiency of detecting the LAMP reaction product was inspected. The results are shown in FIG. 6. In the case of the reaction solutions to which the second intercalator was not added in addition to acridine orange (AO in FIG. 6), the fluorescence intensity of the positive reaction solution was 7,121, and that of the negative reaction solution was 6,195. That is, difference in the fluorescence intensity resulting from the occurrence of products of double-stranded nucleic acid amplification was 926. In contrast, in the case of the reaction solutions to which methylene blue was added (AO+MB in FIG. 6), the fluorescence intensity of the positive reaction solution was 3,500, and that of the negative reaction solution was 350. That is, difference in the fluorescence intensity resulting from the occurrence of products of double-stranded nucleic acid amplification was as large as 3150. In the case of the reaction solutions to which actinomycin D was added (AO+ AD in FIG. 6), the fluorescence intensity of the positive reaction solution was 7,368, and that of the negative reaction solution was 4,762. That is, difference in the fluorescence intensity resulting from the occurrence of products of double-stranded nucleic acid amplification was as large as 2,606. Further, in the case of the reaction solutions to which SYBR Green 2 was added (AO+SYBR-G in FIG. 6), the fluorescence intensity of the positive reaction solution was 9,435, and that of the negative reaction solution was 4,721. That is, difference in the fluorescence intensity resulting from the occurrence of products of double-stranded nucleic acid amplification was as large as 4,714.

Thus, sensitivity for detecting products of double-stranded nucleic acid amplification using acridine orange can be enhanced by performing the LAMP reaction in the presence of the second intercalator together with acridine orange.

EXAMPLE 5

Effect of Methylene Blue On the Detection of the LAMP Reaction Product Using YO-PRO-1®

Figure 7:
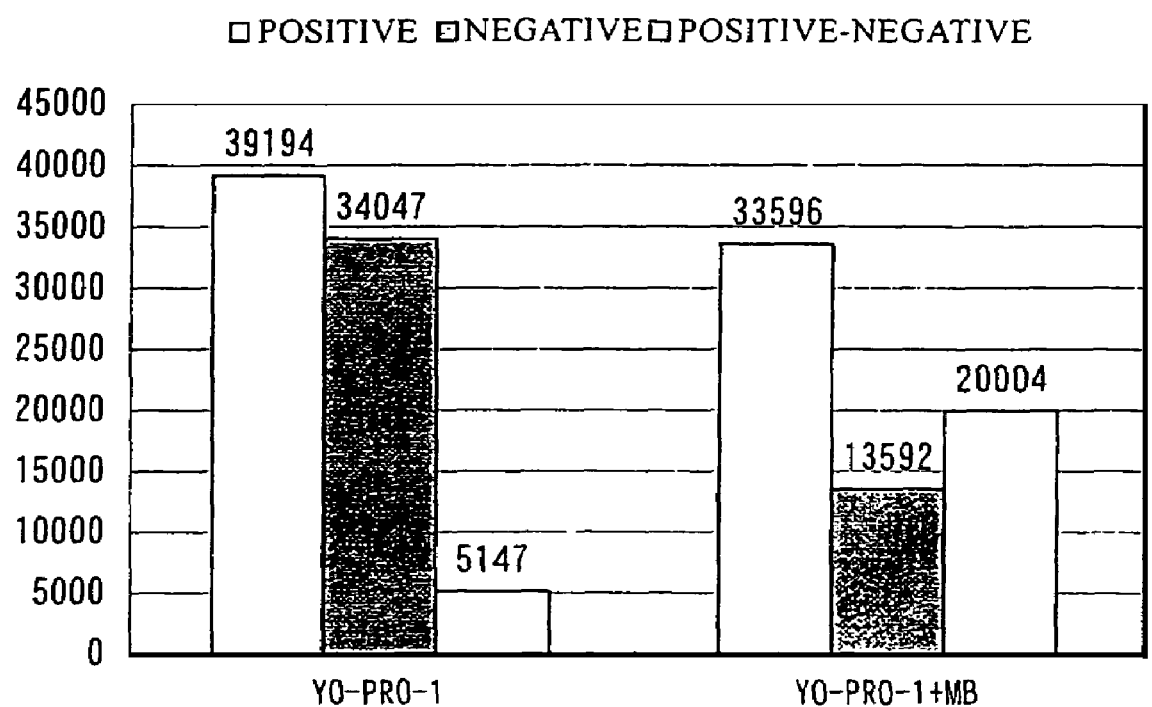
FIG. 7 shows fluorescence intensity of each reaction solution when the LAMP reaction is carried out by adding methylene blue as the second intercalator to YO-PRO-1® (Quinolinium, 4-[(3-methyl-2(3H)-benzoxazolylidene)methyl]-1-[3-(trimethylammonio)propyl]-, diiodide.

The LAMP reaction was carried out under the same reaction conditions as in Example 3 except that 1 μg/ml of YO-PRO-1® and 10 μM of methylene blue as the second intercalators were added instead of ethidium bromide. Thus, the effect of methylene blue on the efficiency of detecting the LAMP reaction product using YO-PRO-1® was inspected. The fluorescence intensity was assayed using 20 μl of the reaction solution after the amplification and a plate reader (Polarion, Tecan) at an excitation wavelength of 485 nm, at an assay wavelength of 535 nm, and at 25° C. The assay results are shown in FIG. 7.

In the case of the reaction solutions to which methylene blue was not added (YO-PRO-1® in FIG. 7), the fluorescence intensity of the positive reaction solution was 39,194, and that of the negative reaction solution was 34,047. That is, difference in the fluorescence intensity resulting from the occurrence of products of double-stranded nucleic acid amplification was 5,147.

In contrast, in the case of the reaction solutions to which methylene blue was added (YO-PRO-1® +MB in FIG. 7), the fluorescence intensity of the positive reaction solution was 33,596, and that of the negative reaction solution was 13,592. That is, difference in the fluorescence intensity resulting from the occurrence of products of double-stranded nucleic acid amplification was as large as 20,004.

Thus, sensitivity for detecting products of double-stranded nucleic acid amplification using YO-PRO-1® can be enhanced by performing the LAMP reaction in the presence of methylene blue as the second intercalator together with YO-PRO-1®.

EXAMPLE 6

Effect of a Complex-forming Compound On the Detection of the LAMP Reaction Product Using Methylene Blue Methylene blue and Acid Orange 7 are mixed in an aqueous solution. This forms a complex. Upon the formation of a complex, the absorption spectrum of methylene blue and that of Acid Orange 7 (AdO) are varied. Thus, the formation of a complex can be confirmed by assaying the absorption spectrum.

Figure 8:
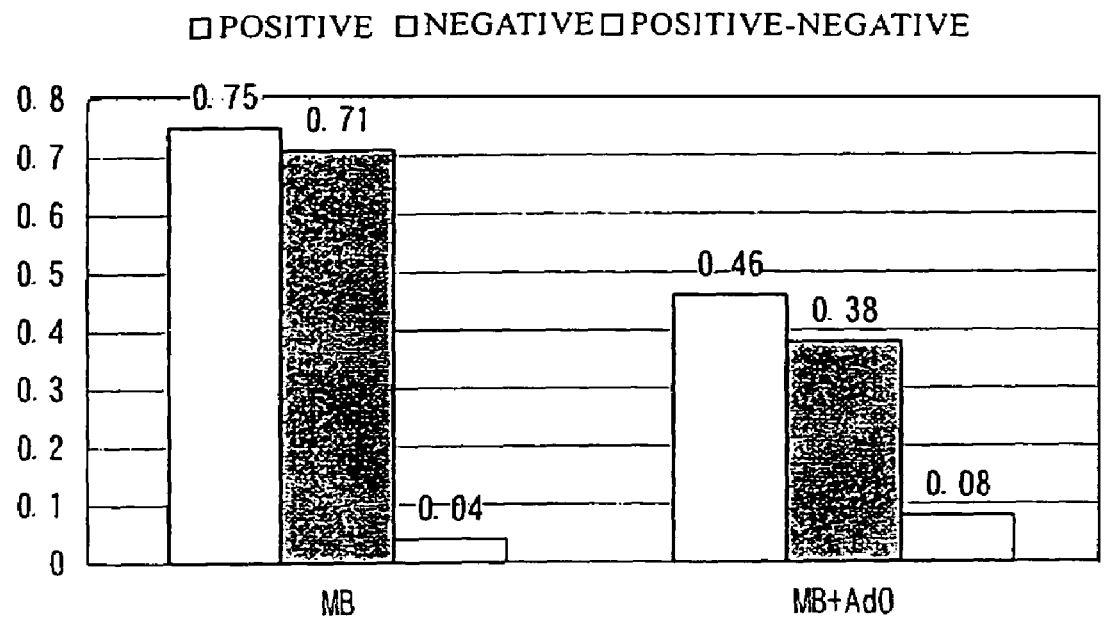
FIG. 8 shows absorbance of each reaction solution when the LAMP reaction is carried out by adding methylene blue and Acid Orange 7.

500 μM of methylene blue or a mixed solution of methylene blue and AdO (500 μM each; methylene blue forms a complex with AdO) was added to the LAMP reaction solution, and the resultant was subjected to nucleic acid amplification in the same manner as in Example 1. The absorbance of the reaction solution after the amplification was assayed using a Shimadzu UV-2200 spectrophotometer (using a 10-mm cell) at the assay wavelength of 680 nm. The assay results are shown in FIG. 8. In the case of the reaction solutions to which AdO was not added (MB in FIG. 8), the absorbance of the positive reaction solution was 0.75, and that of the negative reaction solution was 0.71. That is, difference in the absorbance resulting from the occurrence of products of double-stranded nucleic acid amplification was 0.04. In contrast, in the case of the reaction solutions to which AdO was added (MB+AdO in FIG. 8), the absorbance of the positive reaction solution was 0.46, and that of the negative reaction solution was 0.38. That is, difference in the absorbance resulting from the occurrence of products of double-stranded nucleic acid amplification was 0.08.

This indicates that AdO regulated the insertion of methylene blue into DNA. More specifically, the insertion of methylene blue into single-stranded DNA is weak and thus is inhibited by AdO. On the contrary, the insertion of methylene blue into double-stranded DNA is strong and thus cannot be inhibited by AdO. Thus, methylene blue is considered to be released from a complex.

Therefore, a bond of an intercalator to a single-stranded nucleic acid is preferentially inhibited by the formation of a complex as well as by oxidation or reduction. Thus, the sensitivity of detecting products of double-stranded nucleic acid amplification can be enhanced.

All publications, patents, and patent applications cited herein are incorporated herein by reference in their entirety.

INDUSTRIAL APPLICABILITY

The present invention provides a method for efficiently detecting products of double-stranded nucleic acid amplification. In particular, the application of the present invention to the detection of products of nucleic acid amplification by the LAMP method can effectively reduce background noises, which are derived from single-stranded nucleic acid caused by the use of a larger amount of primers compared with the case of PCR.

Free Text of Sequence Listing
   SEQ ID NO: 1; synthetic DNA
   SEQ ID NO: 2; synthetic DNA
   SEQ ID NO: 3; synthetic DNA
   SEQ ID NO: 4; synthetic DNA
   SEQ ID NO: 5; synthetic DNA

---

What is claimed is:

1. A method for detecting a product of nucleic acid amplification comprising the following steps:
   (a) amplifying a nucleic acid through nucleic acid amplification;
   (b) adding an intercalator to a reaction solution after the nucleic acid amplification;
   (c) reducing signals derived from an intercalator bound to a single-stranded nucleic acid by adding a compound that reacts preferentially with an intercalator bound to a single-stranded nucleic acid as compared to an intercalator bound to a double-stranded nucleic acid to a mixture comprising double-stranded nucleic acid bound to an intercalator and single-stranded nucleic acid bound to an intercalator, thereby reducing signals derived from an intercalator bound to a single-stranded nucleic acid; and
   (d) assaying the fluorescence intensity of a reaction solution.

2. A method for detecting a product of nucleic acid amplification, the method comprising:
   (a) amplifying a nucleic acid through nucleic acid amplification in the presence of an intercalator;
   (b) reducing signals derived from an intercalator bound to a single-stranded nucleic acid by adding a compound that reacts preferentially with an intercalator bound to a single-stranded nucleic acid as compared to an intercalator bound to a double-stranded nucleic acid to a mixture comprising double-stranded nucleic acid bound to an intercalator and single-stranded nucleic acid bound to an intercalator, thereby reducing signals derived from an intercalator bound to a single-stranded nucleic acid; and (c) assaying the fluorescence intensity of a reaction solution.

3. The method for detection according to claim 1, wherein the nucleic acid amplification is carried out by the following steps:
(a) selecting a first arbitrary sequence F1c, a second arbitrary sequence F2c, and a third arbitrary sequence F3c in that order from the 3' terminus in a target region toward the 3' terminus on the polynucleotide chain and a fourth arbitrary sequence R1, a fifth arbitrary sequence R2, and a sixth arbitrary sequence R3 in that order from the 5' terminus in the target region toward the 5' terminus of the nucleotide chain;
(b) preparing a primer containing sequence F2 which is complementary to F2c and, on the 5' side of F2, the same sequence as F1c; a primer containing sequence F3 which is complementary to F3c; a primer containing the same sequence as R2 and, on the 5' side of the sequence, sequence R1c which is complementary to R1; and a primer containing the same sequence as R3; and
(c) synthesizing DNA in the presence of a strand displacement-type polymerase and the primers using the nucleotide chain as a template.

4. The method for detection according to claim 1, wherein the nucleic acid amplification is carried out by the following steps:
(a) selecting a first arbitrary sequence F1c and a second arbitrary sequence F2c in that order from the 3' terminus in a target region toward the 3' terminus on the polynucleotide chain and a third arbitrary sequence R1 and a fourth arbitrary sequence R2 in that order from the 5' terminus in the target region toward the 5' terminus of the nucleotide chain;
(b) preparing a primer containing sequence F2 which is complementary to F2c and, on the 5' side of F2, the same sequence as F1c; and a primer containing the same sequence as R2 and, on the 5' side of the sequence, sequence R1c which is complementary to R1; and
(c) synthesizing DNA in the presence of a strand displacement-type polymerase, the primers, and a melting temperature regulator using the nucleotide chain as a template for amplification.

5. The method for detection according to claim 4, wherein the melting temperature regulator is betaine or trimethylamine N-oxide.

6. The method of claim 1, wherein the intercalator is any of ethidium bromide, acridine orange, TO-PRO-1® (Quinolinium, 4-[(3-methyl-2(3H) -benzothiazolylidene)methyl]-1-[3-(trimethylammonio)propyl]-, diiodide YO-PRO-1® (Quinolinium, 4-[(3-methyl-2(3H)-benzoxazolylidene)methyl]-1-[3-(trimethylammonio)propyl]-, diiodide), or methylene blue.

7. The method of claim 1, wherein the compound that reacts preferentially with an intercalator bound to a single-stranded nucleic acid as compared to an intercalator bound to a double-stranded nucleic acid is an oxidant or reducer.

8. The method of claim 7, wherein the oxidant is any of sodium hypochlorite, hydrogen peroxide, or potassium permanganate.

9. The method of claim 7, wherein the reducer is sodium borohydride or sodium cyanoborohydride.

10. The method of claim 2, wherein the intercalator is any of ethidium bromide, acridine orange, TO-PRO-1® (Quinolinium, 4-[(3-methyl-2(3H) -benzothiazolylidene)methyl]-1-[3-(trimethylammonio)propyl]-, diiodide), YO-PRO-1® (Quinolinium, 4-[(3-methyl-2(3H)-benzoxazolylidene)methyl]-1-[3-(trimethylammonio)propyl]-, diiodide), or methylene blue.

11. The method of claim 2, wherein the compound that reacts preferentially with an intercalator bound to a single-stranded nucleic acid as compared to an intercalator bound to a double-stranded nucleic acid is an oxidant or a reducer.

12. The method of claim 11, wherein the oxidant is any of sodium hyperchlorite, hydrogen peroxide, or potassium permanganate.

13. The method of claim 11, wherein the reducer is sodium borohydride or sodium cyanoborohydride.

14. The method of claim 2, wherein the compound that is bound to a single-stranded nucleic acid more strongly than an intercalator and is bound to a double-stranded nucleic acid more weakly than an intercalator is a second intercalator different from said intercalator.

15. The method of claim 14, wherein the second intercalator is any of methylene blue, actinomycin D, SYBR® Green 2 (CAS Registry No. 172827-25-7) or OliGreen® (CAS Registry No. 268220-33-3).

* * * * *